(12) United States Patent
Ruetenik

(10) Patent No.: US 9,498,638 B2
(45) Date of Patent: Nov. 22, 2016

(54) EQUINE HOOF PULSED ELECTROMAGNETIC FIELD THERAPY SYSTEM AND APPARATUS

(71) Applicant: Monty L. Ruetenik, Clear Lake Shores, TX (US)

(72) Inventor: Monty L. Ruetenik, Clear Lake Shores, TX (US)

(*) Notice: Subject to any disclaimer, the term of this patent is extended or adjusted under 35 U.S.C. 154(b) by 233 days.

(21) Appl. No.: 14/481,574

(22) Filed: Sep. 9, 2014

(65) Prior Publication Data

US 2015/0151136 A1    Jun. 4, 2015

Related U.S. Application Data

(60) Provisional application No. 61/911,606, filed on Dec. 4, 2013.

(51) Int. Cl.
| | | |
|---|---|---|
| *A61N 2/02* | (2006.01) | |
| *A61N 2/00* | (2006.01) | |
| *A01L 15/00* | (2006.01) | |

(52) U.S. Cl.
CPC ............... *A61N 2/004* (2013.01); *A01L 15/00* (2013.01); *A61N 2/02* (2013.01)

(58) Field of Classification Search
CPC ............ A01L 15/00; A01L 1/00–1/04; A01L 3/00–3/06; A01L 5/00; A01L 7/00–7/10; A01L 9/00; A01L 11/00; A61N 2/00–2/12; A01K 13/007
See application file for complete search history.

(56) References Cited

U.S. PATENT DOCUMENTS

| | | | |
|---|---|---|---|
| 4,456,001 A * | 6/1984 | Pescatore | A61N 2/02 600/14 |
| 5,792,040 A | 8/1998 | Koeneman et al. | |
| 6,062,008 A * | 5/2000 | Nor | A01K 13/007 54/82 |
| 6,132,362 A | 10/2000 | Kuo et al. | |
| 6,174,277 B1 * | 1/2001 | Nichols | A61N 2/00 54/82 |
| 8,166,734 B2 | 5/2012 | Ruetenik | |
| 8,220,231 B2 | 7/2012 | Ruetenik | |
| 8,291,683 B2 | 10/2012 | Ruetenik | |
| 2009/0012515 A1 * | 1/2009 | Hoenig | A61B 18/203 606/33 |
| 2010/0031614 A1 * | 2/2010 | Osborne | A01K 13/007 54/82 |
| 2010/0095641 A1 * | 4/2010 | Ruetenik | A01K 13/007 54/82 |
| 2010/0204769 A1 | 8/2010 | Markoll | |
| 2011/0067366 A1 | 3/2011 | Ruetenik | |

OTHER PUBLICATIONS

Marko S. Markov; Pulsed electromagnetic field therapy history, state of the art and future; Environmentalist DOI 10.1007/s10669-007-9128-2; 2007.
David W. Ramey, DVM; Magentic and Electromagnetic Therapy in Horses ; http://www.veterinarywatch.com/MAG.htm.
Pulsed electromagnetic field therapy; http://en.wikipedia.org/wiki/Pulsed_electromagnetic_field_therapy; 1990.
Harmonic Frequency Stimulator (HFS) Technology; http://www.althealing.pemf-equine.us/and    http://www.horsetherapyllc.com/pemf.php.
PEMF Design Proposal; 2013.

* cited by examiner

*Primary Examiner* — Charles A Marmor, II
*Assistant Examiner* — Thaddeus Cox
(74) *Attorney, Agent, or Firm* — Douglas Baldwin

(57) ABSTRACT

Disclosed is an assembly or system and apparatus for applying pulsing electromagnetic field (PEMF) coils to the underside of an equine hoof. The PEMF coil is encased in an elastomer structure to form a "puck" that will protect the coils from moisture, dirt and damage from rough use. The coil, and preferably a puck containing the coil may suitably be placed on, in or under an elastomeric orthotic pad that is disposed in a suitable equine boot.

12 Claims, 6 Drawing Sheets

EQUINE HOOF PULSED ELECTROMAGNETIC FIELD THERAPY SYSTEM AND APPARATUS

CROSS REFERENCE TO RELATED APPLICATIONS

This application claims benefit of Provisional Application Ser. No. 61/911,606 filed Dec. 4, 2013, the content, Figures and disclosure of which are incorporated herein by ref

FIELD OF INVENTION

Apparatus and system for the application of pulsed electrometric field (PEMF) therapy to an equine hoof.

BACKGROUND

The benefits of pulsed electrometric field (PEMF) therapy in animals and humans is well documented. As described in Wikipedia, "Pulsed electromagnetic field therapy (PEMF) is a reparative technique most commonly used in the field of orthopedics for the treatment of non-union fractures, failed fusions, congenital pseudarthrosis and depression. In the case of bone healing, PEMF uses electrical energy to direct a series of magnetic pulses through injured tissue whereby each magnetic pulse induces a tiny electrical signal that stimulates cellular repair. Many studies have also demonstrated the effectiveness of PEMF in healing soft-tissue wounds; suppressing inflammatory responses at the cell membrane level to alleviate pain, and increasing range of motion. The value of pulsed electromagnetic field therapy has been shown to cover a wide range of conditions, with well documented trials carried out by hospitals, rheumatologists, physiotherapists and neurologists. There are several electrical stimulation therapy devices, approved by the FDA, that are widely available to patients for use. These devices provide an additive solution that aid in bone growth repair and depression." See en.wikipedia.org/wiki/Pulsed_electro-magnetic_field_therapy.

PEMF has long been used in equine and other animal therapy and a number of companies sell PEMF units for equine treatment. It is said that PEMF therapy regenerates damaged and diseased tissue, repairs torn tendons and fractured bones; enhances the synthesis of protein in the cells allowing the body to take advantage of all the protein available; improves circulation not by increasing heartbeat or blood pressure but by opening and dilating the arteries and capillaries; and increases the cellular level of oxygen absorption. Studies have shown that oxygen partial pressure can be increased by 200%. This reduces pain associated with lack of sufficient oxygen. Also, insufficient oxygen in the cells causes lactic acid buildup under strenuous exercise. Information on the history and operations of PEMF can be found in: Markov, Marko S.: *Pulsed w electromagnetic field therapy history, state of the art and future*; Environmentalist, 2007 and Ramsey, David W.; *Magnetic and Electromagnetic Therapy in Horses*; See article at www.veterinarywatch.com/MAG.htm.

These references are included in the Information Disclosure Statement provided with this application.

PEMF has not, to the knowledge of Applicant, to date been applied equine hooves, but the benefits in so doing should match those of soft tissue and bone therapies and increase blood circulation and enhance healing and growth of hoof tissue.

DESCRIPTION OF FIGURES

The Figures represent embodiments and aspects of the invention and are not intended to be limiting of the scope of the invention.

DETAILED DESCRIPTION

In broad scope this invention is an assembly or system and apparatus for applying pulsing electromagnetic field (PEMF) coils to the underside of an equine hoof. PEMF systems consist of an application coil electrically attached to a pulse electrometric generator. The PEMF coil is preferably encased in an elastomer structure to form a "puck" that will protect the coils from moisture, dirt and damage from rough use. The coil, and preferably a puck containing the coil may suitably be placed on, in or under an elastomeric orthotic pad that is disposed in a suitable equine boot.

Figure 1:
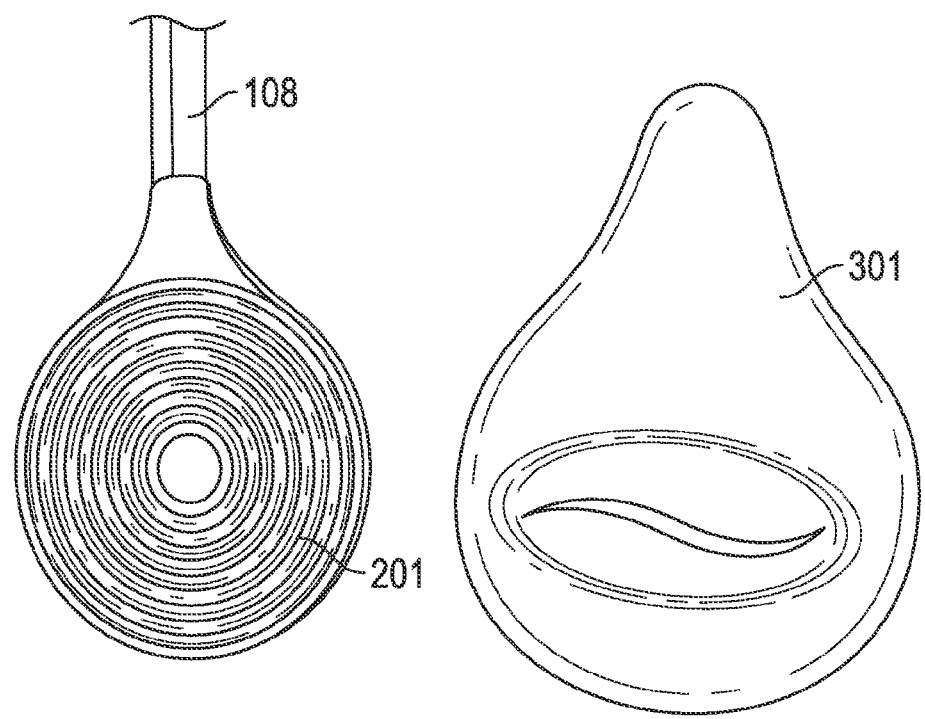
FIG. 1 is a schematic view of the PEMF coils and a schematic view of the coils incased in an elastomer structure ("puck") of an embodiment of the invention.
Figure 4:
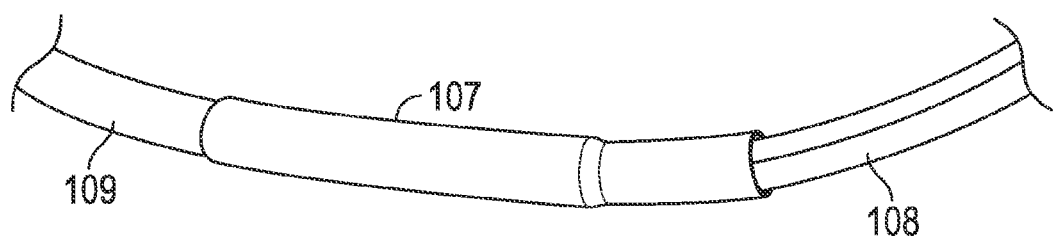
FIG. 4 is a schematic view of the leads from a coil merged into a single insulated casing illustrative of an aspect of an embodiment of the invention.

In one embodiment the application PEMF coil is two layers of coils arrangement with about 6 to 18 insulated coil turns in each of two attached coil layers (FIG. 1—item 201) with electrical connections (108) extending from each end of the coil. FIG. 1 illustrates an embodiment of the coil arrangement 201 and 108. The structure 301 is the coil 201 encased in an elastomer (preferably polyurethane) preferably having a Shore A hardness of from about 30 to 90. The coil is typically about number 12 insulated wire. Other sizes could be used but the number 12 wire works well. The electrical wire extensions from the coil are connected to an electromagnetic pulsing device that is not a part on the present invention. The configuration of the coil leads is shown in FIG. 4 where 109 is two coils in an insulation sheaf, 107 is an expanded strengthening wrap and 108 are the coils. PEMF systems are available from a number of companies including: Equipulse from Magnus Magnetic LLC; Respond Systems; Curavet, Ltd; and Centurion.

Figure 10:
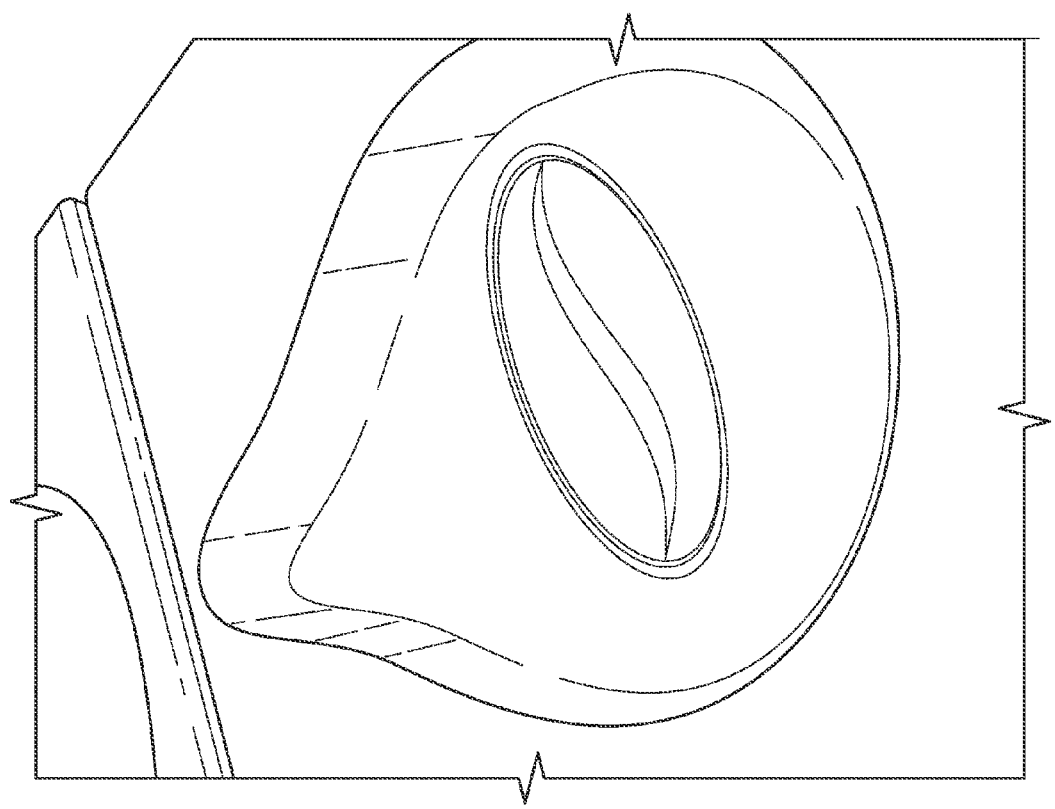
FIG. 10 is a schematic view of a mold for encasing a coil in elastomer polymer.

A puck may be made by placing it in an appropriate configured mold into which is poured polyurethane (or other moldable polymer) of a composition to yield a suitable elastomeric molded part. A suitable mold is shown in FIG. 10.

Figure 2:
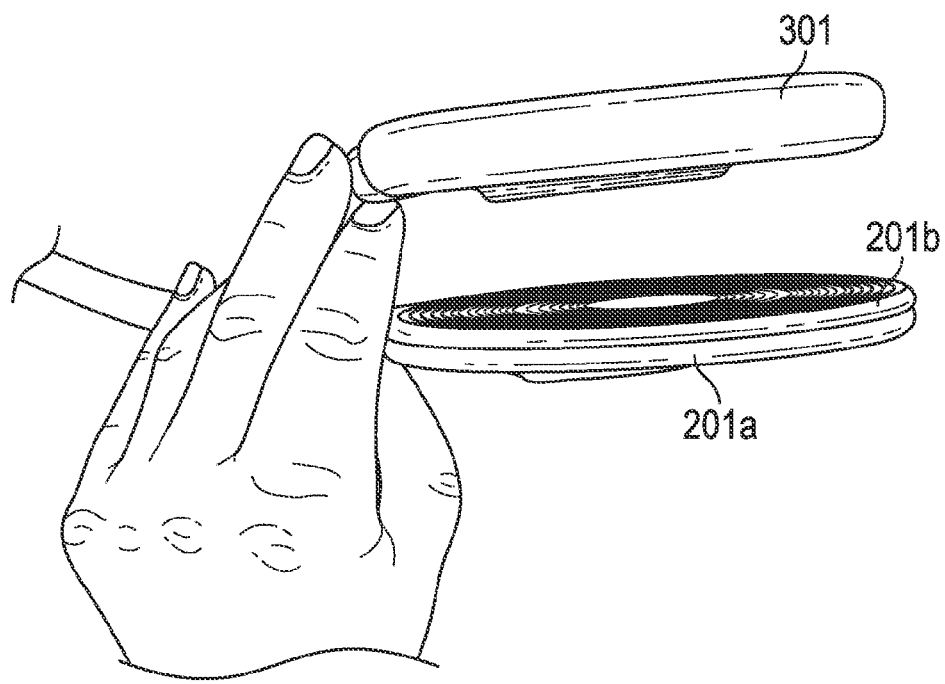
FIG. 2 is a schematic view of a side view of the PEMF coils and a of a side view of the coils encased in an elastomer puck of an embodiments of the invention.

FIG. 2 shows the relative thickness of the two layer coil and a puck. In a prototype of the invention the coil stack is less than about ½ inches thick and the puck is about ⅜ inches thick. The puck is about 4½ inches in diameter on the short diameter. The size will be determined by the size of the boot into which it is to be disposed that in turn is determined by the hoof size.

Figure 3:
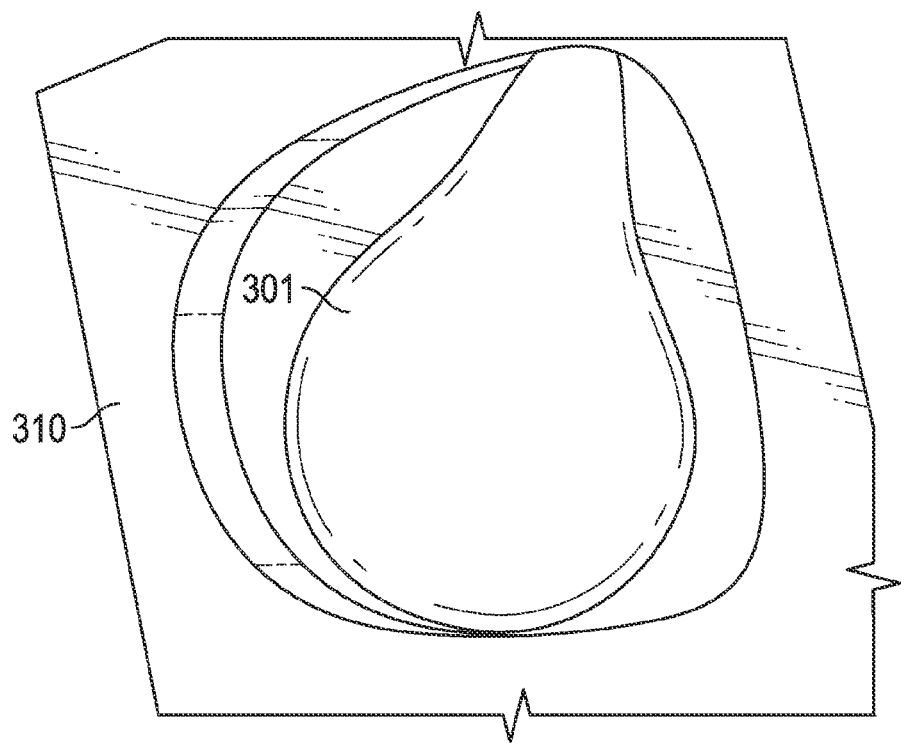
FIG. 3 is schematic view of a puck disposed in an elastomeric pad cavity.
Figure 6:
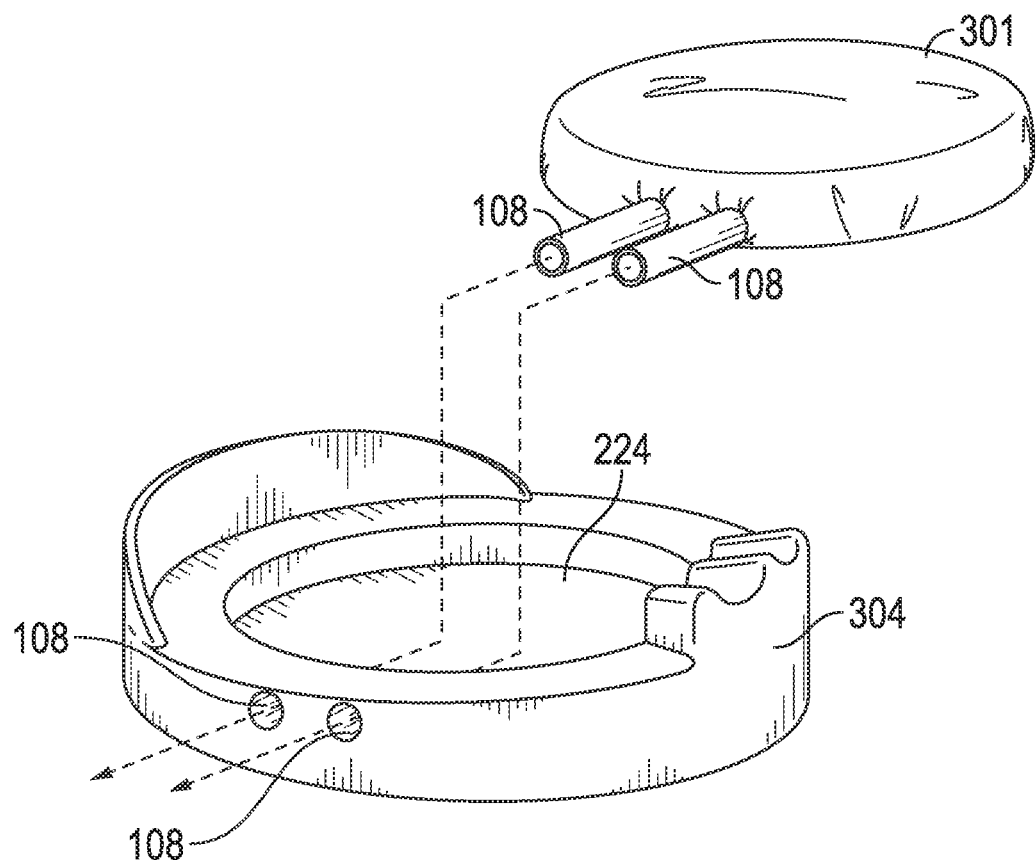
FIG. 6 is a schematic of an orthotic pad having a cavity for a removable coil puck.
Figure 7:
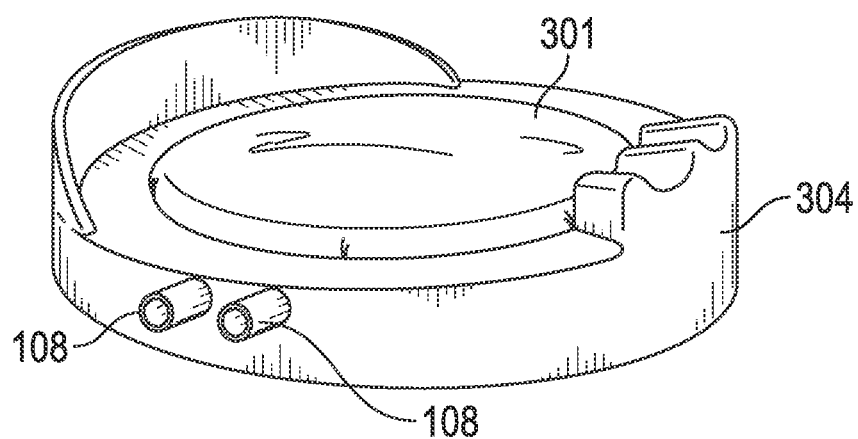
FIG. 7 is a schematic showing the removable coil puck resting in the orthotic cavity.
Figure 8:
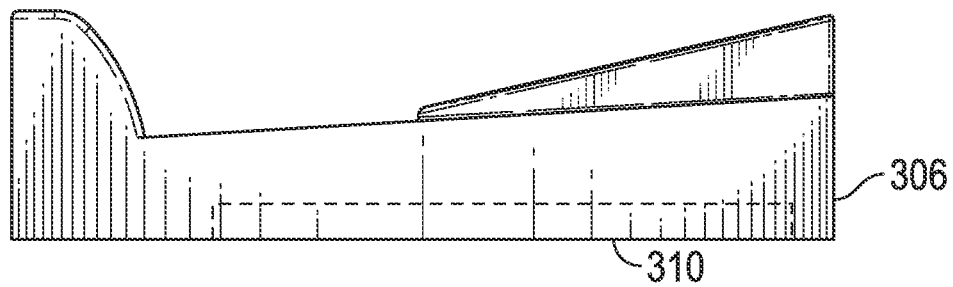
FIG. 8 is a side view of an orthotic pad showing a cavity (dotted lines) for a removable puck.
Figure 9:
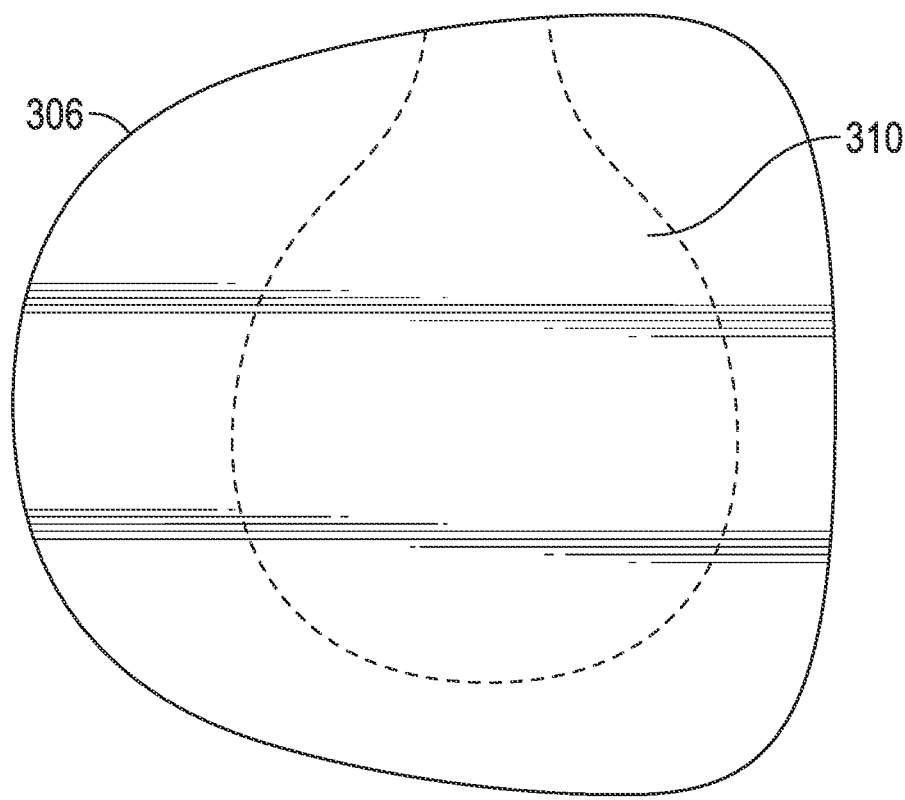
FIG. 9 is a side view of an orthotic pad showing a cavity (dotted lines) for a puck.

The coil or puck is suitably disposed in an elastomeric orthotic pad which is placed in the bottom of an equine boot. FIGS. 3 and 6-9 show possible arrangements of a puck in an orthotic pad. In FIG. 3 the puck 301 in disposed in pad 310. In FIG. 6 pad 304 has a cavity 224 into which puck 301 is placed. Item 108 are the electrical leads. FIG. 7 is the same as FIG. 6 showing the puck 301 placed in the cavity 224. These Figures show the cavity approximately centered in the pad but it is preferred that the puck be placed toward the rear of the pad (where 304 is pointing) as can be seen in the bottom cavity (310) of FIGS. 8 and 9. The above described pad cavity descriptions provide arrangements in which the puck can easily be removed and replaced without replacement of the orthotic pad and allows different configurations of coil and puck to be used. It will be desirable in some cases to have the orthotic pad thicker than the puck so that the hoof rests on the peripheral circumference of the soft gel pad. It is also an aspect of the invention to completely encase the puck or just the coil in the orthotic pad as by molding it into the pad as the pad is being made. This provides a more permanent and perhaps more stable positioning of the coil and enhances the protection of the coil (or puck) from damage.

Figure 5:
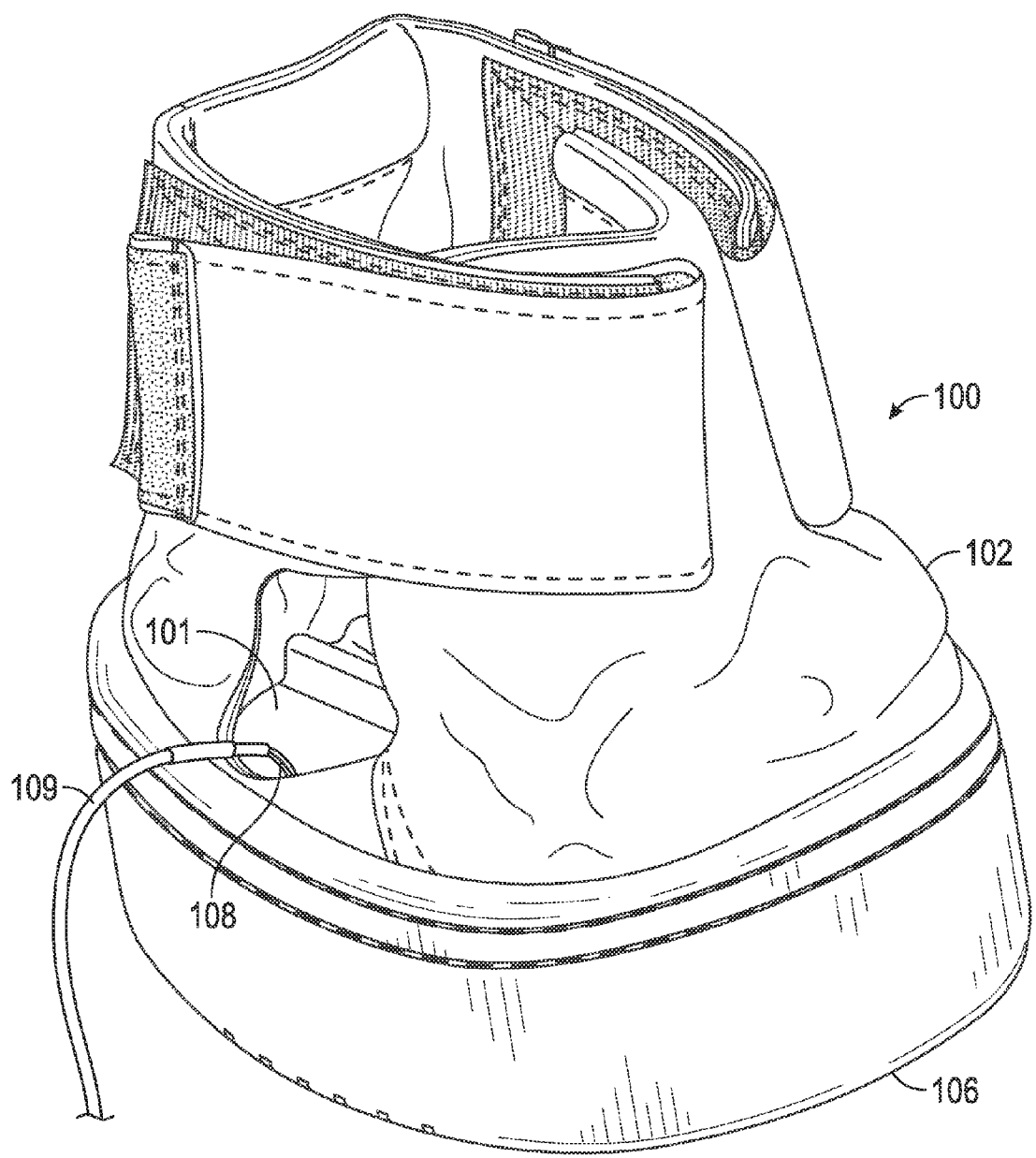
FIG. 5 shows a schematic view of an equine boot assembly showing how coil leads extend from a coil disposed in, on or under an elastomeric orthotic pad in the boot assembly.

In another aspect the invention is an assembly comprising a coil disposed in an elastomeric casing to form a puck that is placed on, in or under an elastomeric orthotic pad placed in an equine boot. Such assembly is illustrated in FIG. 5, where boot 100 has a fabric upper 102, side openings 103, an orthotic pad 101. The fabric upper 102 is connected to a sole plate 106 which has an upward projecting wall that completely surrounds the circumference of the sole of the boot. The fabric extend inside the sole plate and covers the inside bottom. It is preferred the orthotic pad a have one side of a hook and loop strap that engages a matching hook and loop strap attached to the fabric at the bottom of the boot. This keeps the pad from rotating when in use on an equine hoof. In the arrangement where the puck is disposed under the pad as in FIGS. 8 and 9 the puck will have a hook and loop strap attached on the underside.

The elastomer orthotic pad may be made of any suitable shock absorbing material such as elastomeric polymer material that provides flexibility, shock absorbency, some degree of elasticity, resilience and has dimensional stability. Polyvinyl chloride PVC, polysilicone and similar elastomers are also suitable. In a preferred embodiment, the base is constructed of a cast polyurethane elastomer. For example, polyurethane-casting elastomer having a Shore A hardness of from about 0 to about 80 is suitable.

Very suitable and preferred equine boots and boot pad assemblies are described in detail in U.S. Pat. No. 7,178,321, U.S. Pat. No. 7,445,051, U.S. Pat. No. 8,220,231 and application U.S. Ser. No. 13/014,535, now U.S. Pat. No. 8,291,683 issued Oct. 23, 2012. The disclosures and figures of these patents are incorporated herein by reference for all purposes.

A suitable and effective sole plate for the boots is described in detail in U.S. Pat. No. 8,220,231 issued Jul. 17, 2012. Similar suitable sole plates are described and shown in; US 2011/00673661 published Mar. 24, 2011; US D565, 256 issued Mar. 25, 2008 and US D616, 614 issued May 25, 2010. The descriptions and Figures of these applications and patents are incorporated herein by reference for all purposes.

A hook-and-loop strap connects to the orthotic pad to mate with a matching hook-and-loop strap on the inside bottom of the sole plate are described U.S. Pat. No. 8,220,231 issued Jul. 17, 2012; US published application 2011/0279184 and, published Mar. 24, 2011, the disclosures and appropriate Figures of which are incorporated herein by reference.

The boots described in the above references, particularly in published applications US 2007/0107389 and US 2011/0067366 are especially preferred since they describe a boot/orthotic pad assembly with a unique combination of beneficial features. In general, the boots described in the above cited applications comprise an upper portion made from flexible material shaped to fit the hoof of an animal and of a height to reach above the hoof of the animal for which it is designed. The boot has a front, sides, rear and bottom; the front slopes back and upward, the sides are lower than the front and rear so that when the front and rear are pulled together here is an opening in the sides. There is a fastening means at the top front and rear to fasten the front and rear together around the leg of a horse. The fabric bottom is attached to a more rigid sole plate comprising a molded elastomer base entirely circumscribed by a peripheral wall (or sides) defining a receiving area sized to fit over (or under) the bottom of the upper portion; said sole plate being securely attached to the lower circumference of the upper portion.

The sole plate of the boot is a preferably a separate molded piece and is attached to the bottom of the fabric upper. The sole plate helps to hold the boot in position on the hoof, and if walled around the entire circumference it prevents the hoof sliding forward or rearward while in use. Moreover, the sole plate is important in confining an elastomeric deep gel pad in place. If a relatively "soft" pad is used (as is often desirable) the weight of the horse will flatten the pad and, if there were an opening in the sole plate wall the pad would be extruded out the opening. In this case it is especially important that the bottom circumference of the boot be sufficiently strong to contain the soft pad when it is squeezed outwardly by the pressure of the horses' hoof. By having the sole plate wall entirely surrounding the circumstance the pad is held in place and will conform to the shape of the hoof and adapt to the shape of the hoof as the horse shifts position or moves. This allows the horse to find the best natural balance position—similar to the effect of having the horse stand in loose sand. The ability to achieve natural balance is especially important for horses with injured or diseased hoofs.

The sole plate is attached to the bottom of the fabric boot. In a preferred embodiment the bottom of the sole plate is sloped upward in the front at an angle of about five (5) to thirty (30) degrees from the bottom plane. The slope begins at a point on the bottom of the soleplate twenty (20) to forty (40) percent of the length from front to rear of the sole plate. The point of beginning is preferably about ⅓ of the distance from the front of the length of the sole plate. This angled sole plate allows the horse hoof to rock forward and backward without undue pressure on the hoof. When the horse walks the boot will "break-over" in a natural way, preventing abnormal pressure on the hoof. This rocker effect is well recognized as beneficial and there are a number of commercial products, such as the "clog" and other devises designed to "rock" with the shift in body weight of the horse allowing it to achieve a "natural balance". This semi rigid boot sole has an advantage over soft or slipper boots since it allows the horse the stability of a flat platform as well as moving the break-over point rearward at the most critical point in the arc of the swinging limb. The front tapered sole plate plus the rocker attachment provides a kind of double break-over point that provides the horse a "restful" stable platform while eliminating the high load point of its stride, especially important and more pronounced when the horse is moving forward and turning. The rotating torque during turning is when lameness shows up most and when the most damage to the lamina connective tissue occurs.

The sole plate is preferably molded of polymeric elastomer material or hard rubber (having the consistency and hardness to approximate automobile tires). Thermoplastic polyurethanes (TPUs) are suitable materials for the base plate. It is preferred that thermoplastic polyurethanes of about 55 to 75 Shore A hardness be used, with Shore A hardness of 65 to 70 being especially suitable. Other polymer materials with similar characteristics as thermoplastic polyurethanes are also usable. Choice of these will be well within the ability of those skilled in the polymer art to select.

The base of the elastomeric deep gel pad is generally shaped to approximate the shape of the animal's hoof print. This pad, made of shock absorbing material can be easily trimmed to conform to the hoof of the individual animal on which it will be used. In one embodiment, on the backside of the base, opposite the ridge, is a frog support. This is a triangular projection above the surface of the base. This triangular projection is designed to approximately correspond to the shape and location of the frog of a horse's hoof. It has been found that the height of the frog support from the sole is very important to provide adequate uniform pressure as well as cushioning of the hoof. This frog support provides increased blood flow to the leg of the animal. The function of the triangle projection is to contact the frog during use, to provide a kind of massage to the frog of the hoof. Thus, blood circulation is stimulated and stress on the animal's legs and tendons are relieved. It is well known that the hoof frog acts somewhat as a blood pump. See for example, U.S. Pat. No. 4,981,010 where it is stated "The horny frog (58) is very elastic and acts as a shock absorber and as a second heart to the horse. As the hoof is pressed against the ground, old blood is forced up and out of the foot. When the hoof is lifted off the ground, the elastic frog (58) springs back, letting new blood into the foot." The frog support aids in this blood circulation. It is this pumping action of the frog that makes the cooling of the sole of the hoof especially effective.

In other embodiments, the pad will not have the triangular projection or the front projection. When used with a horse that has an abscessed or injured frog it may be desirable to use a pad without the frog support. Also the improved sole plate of the boot makes it is possible to eliminate the front projection for some applications. However, even without the frog support the front ridge projection is often useful, especially for a horse with a severely injured or damaged hoof. At times it is necessary to resection (remove the front hard hoof surface) a horses hoof if it is damaged or diseased. Such is the case with advanced laminitis. In such cases the soft front support ridge provides extra comfort to the hoof, especially if the pad is wedged shaped (sloped) in a way that forces the front of the hoof downward. It is the burden of the base of the pad to supply the bulk of the support for the animal. The frog support is an aid to stimulation of the frog and is not the principal means of supporting the hoof. In this way, the present invention differs from previous frog support shoes or pads. The relative large and soft pad of the present invention enables the horse to adjust the position of its hoof to the most comfortable position.

It has also been found that the shape of the pad is important. Round pads have been found to not perform well in actual use as slightly elliptical pads; they tend to rotate in the boot. An elliptical shaped pad is desirable to maintain consistent fit and to prevent rotation in the pad in use. The pad is shaped to fit the configuration of the equine hoof; many horses have hoofs that, while elliptical are more nearly round. Arabian horses, as well as horses that have elongated "toes" due to injury, disease or otherwise, have narrower hoofs so the elliptical shape is more pronounced.

The base of the gel pad is made of any suitable elastomeric polymer material that provides flexibility, shock absorbency, some degree of elasticity, resilience and has dimensional stability. Polyvinyl chloride PVC, polysilicone and similar elastomers well known to those in the art are also suitable. In a preferred embodiment, the base is constructed of a cast polyurethane elastomer. For example polyurethane-casting elastomer having a Shore A hardness of from about 10 to about 70 is suitable. It is preferred that the base be of about 20 to 70 Shore A hardness and the support be of about 8 to 50 Shore A hardness. In one embodiment, very soft pads are desirable. These should be thicker than harder pads and will have a Shore 00 hardness of about 5 to 70.

For the pads of this invention it is preferred that the pad material have low rebound resiliency, generally lower that twenty five (25) percent, and more desirably between two (2) and ten (10) percent.

When the PEMF coils are disposed in one of the above described boot/pad assemblies it provides not only the benefits of the boot pad assembly but the additional therapeutic benefits of the PEMF treatment.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An assembly for applying pulsing electromagnetic field (PEMF) coils beneath an equine hoof comprising a pulsing electromagnetic field treatment coil encased in an elastomer structure, disposed in an equine boot wherein the pulsing electromagnetic field treatment coil has 6-18 turns to form complete loops and has connection means on each end of the coil for connection to a pulsing electromagnetic field generator.

2. The assembly of claim 1 wherein the elastomer structure is polyurethane.

3. The assembly of claim 1 wherein the coil comprises at least two layers of PEMF coils placed substantially on top of each other.

4. The assembly of claim 1 comprising an equine boot having disposed therein a removable elastomeric orthotic pad having a top side and underside and wherein there is disposed on, or in or under the orthotic pad a pulsing electromagnetic field treatment coil encased in an elastomer structure.

5. The assembly of claim 4 wherein the encased coil is disposed in a cavity on the underside of the orthotic pad.

6. The assembly of claim 4 wherein the equine boot comprises an upper section made from flexible material and an enclosed bottom section, the upper section shaped to fit around the hoof of a horse and of a height to reach above the hoof of a horse, having a front, sides, and rear, a fastening means to fasten the front and rear together around a leg of a horse, and a bottom section made of an elastomer attached to the upper section of sufficient height and strength to constrain the deformation of a cushioning pad placed therein and compressed by the weight of a horse's hoof; and an elastomer orthotic pad of Shore 00 hardness of between 5 and 70 disposed over the bottom section of the equine boot.

7. The assembly of claim 4 wherein the equine boot comprises a removable elastomeric shock absorbing pad disposed inside the boot and having a pressure pulsing means disposed under or within the shock absorbing pad.

8. The assembly of claim 7 wherein the removable shock absorbing pad is elastomeric and has the pressure pulsing means molded as an integral part of the elastomeric shock absorbing pad.

9. The assembly of claim 7 wherein the pressure pulsing means is connected to a pressure source for inflating the pulsing means and a pressure relief means to release pressure and thereby deflate the pulsing means.

10. The assembly of claim 1 wherein the encased coil is entirely enclosed in an elastomeric orthotic pad.

11. The assembly of claim 10 wherein the orthotic pad is made of polyurethane and the coil is encased in polyurethane.

12. The assembly of claim 1 also comprising a pulsing electromagnetic field (PEMF) generator connected to the PEMF coils.

* * * * *